(12) United States Patent
Diaz et al.

(10) Patent No.: US 6,462,210 B1
(45) Date of Patent: Oct. 8, 2002

(54) FRACTIONATION PROCESS FOR THE UNSAPONIFIABLE MATERIAL DERIVED FROM BLACK-LIQUOR SOAPS

(75) Inventors: Miguel Angel Fuenzalida Diaz; Alejandro Markovits Rojas, both of Santiago (CL)

(73) Assignee: Harting, S.A., Santiago (CL)

( * ) Notice: Subject to any disclaimer, the term of this patent is extended or adjusted under 35 U.S.C. 154(b) by 0 days.

(21) Appl. No.: 09/293,282

(22) Filed: Apr. 16, 1999

(51) Int. Cl.[7] .............................. C07J 9/00; B01D 3/00
(52) U.S. Cl. ........................... 552/545; 203/71; 203/81
(58) Field of Search ..................... 552/545; 203/71, 203/81

(56) References Cited

U.S. PATENT DOCUMENTS 2,591,885 A * 4/1952 Cleary et al. .............. 260/419
2,716,630 A * 8/1955 Spangenberg et al. ........ 202/52
4,524,024 A * 6/1985 Hughes ...................... 260/97.6
4,524,030 A * 6/1985 Cleary et al. ............... 260/419

OTHER PUBLICATIONS

Addison Ault, "Techniques and Experiments for Organic Chemistry." 2nd edition, Section 8, Distillation, pp. 29–41, 1976.*

* cited by examiner

Primary Examiner—Barbara P. Badio
(74) Attorney, Agent, or Firm—Baker & McKenzie (57) ABSTRACT

The present invention relates to a fractionation process of the unsaponifiable material derived from black-liquor soaps of the cellulose industry. Through this procedure fractions that essentially contain free sterols, fatty alcohols, sterol esters and fatty alcohol esters respectively are separated. Fractions containing sterols or fatty alcohols can be used as such in the alimentary, cosmetic and pharmaceutical industries or they can be used as raw materials for transforming into other useful products.

16 Claims, 2 Drawing Sheets

FRACTIONATION PROCESS FOR THE UNSAPONIFIABLE MATERIAL DERIVED FROM BLACK-LIQUOR SOAPS

BACKGROUND OF THE INVENTION

1. Field of the Invention

The present invention relates to a fractionation process of the unsaponifiable material derived from black-liquor soaps of the cellulose industry. Through this procedure fractions that essentially contain free sterols, fatty alcohols, sterol esters and fatty alcohol esters respectively are separated. Fractions containing sterols or fatty alcohols can be used as such in the alimentary, cosmetic and pharmaceutical industries or they can be used as raw materials for transforming into other useful products.

2. Description of the Related Art

Black-liquor soaps are by-products of the Kraft pulping process of pine and other woods. Typically, during the Kraft process, wood chips are digested or cooked for two hours at 170° C. in an aqueous liquor containing sodium hydroxide and sodium sulfide. The digestion delignifies the wood chips and gives rise to a dark aqueous suspension called black liquor which along with lignin contains cellulose pulp, sodium soaps of rosin acids and fatty acids, a series of neutral organic compounds such as sterols, terpene, fatty alcohols, sterol esters, fatty alcohol esters and products of lignin degradation. Under these conditions, the cellulose is stable and remains in suspension in the black liquor. When the pulping process reaction is finished, the cellulose pulp is separated from the black liquor and is washed. The pulp can be used as such or exposed to further purification processes.

The black liquor must be recovered for both economics and environmental reasons. To this end, the black liquor is typically concentrated by evaporation to a solid content from 23 to 32% in weight of black liquor solids. This causes the separation of fatty acid soaps and rosin soaps and also other hydrophobic compounds solubilized in the soaps. The soaps float at the top of the vessel where they are removed or skimmed off, hence they are called "skimming". Skimming is the term that we are going to use as a synonym of black liquor soaps. Other names used to denominate this fraction are "tall oil soap" or "CSS" (Crude Sulfate Soap).

The skimming contains ordinarily between 30 and 50% of water. The skimming solids are a complex mixture of sodium fatty soaps and rosin acids, and a series of hydrophobic substances essentially composed of sterols, stanols, fatty alcohols, diterpenoids, sterol esters and fatty alcohol esters with fatty acids. These hydrophobic compounds are known as the neutral unsaponifiable fraction or unsap. Sometimes these unsaps constitute up to 25% of the skimming solids.

The skimming may be used as fuel oil; its calorific value is lower than the half of the fuel oil calorific value. It may be upgraded by transforming into tall oil with sulfuric acid and separating the oil from the aqueous phase. This oil is known as crude tall oil (CTO). Then CTO is exposed to a series of vacuum distillations which produce: fatty acids, TOFA or Tall Oil Fatty Acids, (these are the most valuable product obtainable from CTO); rosin acids or TOR (Tall Oil Rosins); DTO or Distilled Tall Oil, which has many industrial uses and PITCH that is the bottom of the distillation, which is used as fuel or as an ingredient for the preparation of asphalt emulsions.

Until recently, improvement in CTO quality was the major reason for refining or separating the unsaponifiable fraction.

Nowadays, there has been a revaluation of unsaps as a source of important chemical products such as sterols, stanols, superior alcohols (notably docosanol and tetracosanol) and their respective esters. They are increasingly applied in the pharmaceutical, cosmetic and alimentary industry.

The refining processes of soaps and the extraction of neutral or unsaponifiable material are widely known in the state of the art and involve the extraction of unsaponifiable material with organic solvents, including supercritical solvents. However, fractionation procedures of these unsaps exhibit a series of technical and economic drawbacks.

Table I shows the average chemical composition of unsaps used in the present invention derived from skimmings of domestic cellulose industries.

The group of components called "others" is mainly composed by terpenoids (mono and diterpenes and its by-products) and betulaprenols and an additional series of insufficiently characterized compounds.

Most identified components of unsaps in Table I are compounds of commercial interest. Sterols, either free or esterified, have many uses as raw material in the pharmaceutical, cosmetic and fermentation industries for transforming into steroids. Sterol esters have been revealed as important antitumor-like agents and their utilization for that purpose is described in U.S. Pat. No. 5,270,041. The reduced form sterols, or stanols, has an important application in the formulation of diets for the reduction of plasmatic cholesterol levels. The use of free stanols for that purpose appears in U.S. Pat. No. 5,244,887, and the utilization of ester stanols for the same purpose appears in U.S. Pat. No. 5,502,045.

There is an increasing interest about fatty alcohols, especially docosanol and tetracosanol, due to their notable pharmacological properties as both anti-inflammatory and antiviral agents. The use of these alcohols with pharmacological purposes appears in many US patents (U.S. Pat. Nos. 4,874,794; 3,031,376; 5,534,554; 5,071,879; and 5,166,219).

At present, the methods known for separating the valuable components of unsaps derived from black liquor soaps or skimming are, hardly without any exception, several variants to dissolution and recrystallization processes. One of the disadvantages of this technique is that it only allows recovering free sterols, remaining the valuable fatty alcohols and alcohol and sterol esters in the mother liquor and they can not be fractionated through liquor recrystallization. By this means, not only the valuable fatty alcohols are not used but also the sterol esters. As a cause of this, the sterol preparation obtained by the methods known in the state of the art is deprived of an important sterol that is mainly found in an esterified form in the unsaps (stigmasterol) and a significant quantity of stigmastanol and sitostanol. The latter is identified as one of the most active and important sterols in the reduction of plasmatic cholesterol levels as it is disclosed in the application PCT/CA95/00555 and U.S. Pat. No. 5,502,045.

TABLE I

Unsaps average composition

| Compound | Weight % |
|---|---|
| 3,5-sitostadiene-3-ona | 0.6 |
| 4-stigmasten-3-ona | 0.5 |

TABLE I-continued

Unsaps average composition

| Compound | Weight % |
|---|---|
| α-Sitosterol | 0.6 |
| β-Sitostanol | 7.5 |
| β-Sitosterol | 21.0 |
| Campestanol | 0.6 |
| Campesterol | 2.1 |
| Cycloartenol | 0.5 |
| Docosanol | 4.4 |
| Eicosanol | 3.6 |
| Ergosterol | 0.2 |
| Escualene | 1.6 |
| Fatty alcohol esters | 6.1 |
| Sterol esters | 13.7 |
| Hexacosanol | 0.2 |
| Methylencycloartenol | 0.4 |
| Pimaral | 0.7 |
| Pimarol | 2.1 |
| Stigmasta-3-ona | 0.3 |
| Tetracosanol | 2.5 |
| Others | 30.8 |

To illustrate what was mentioned above, Table II shows the sterol composition in the unsap fraction composed by esters. Through the procedure of this invention described below, these esters are separated from other unsaps components, then they are hydrolyzed and exposed to a chromatographic analysis, resulting the following results:

TABLE II

Relative composition of esterified sterols in the unsap

| Sterol | % Relative |
|---|---|
| β-Sitostanol | 41.6 |
| Campestanol | 6.6 |
| Campesterol | 1.6 |
| Stigmasterol | 36.6 |
| Others | 13.3 |

The separation of the ester fraction from unsaps and its further hydrolysis surprisingly discloses the presence of sterols in the unsaps like stigmasterol which is not normally detected.

There are many patents that disclose the different methods of the unsap fractionation technique.

U.S. Pat. No. 4,044,031 discloses a dissolution method of unsaps in a solvent mixture, which includes hexane-acetone-methanol, followed by a process of liquid-liquid extraction using a hexane-acetone-water mixture. The extract is concentrated and then is cooled down to obtain a sterol concentrate through crystallization.

U.S. Pat. No. 4,420,427 discloses a method by which the unsaps are exposed to a hot dissolution with methyl ethyl ketone or with a mixture of methanol with methyl ethyl ketone. Then, by cooling down the mixture, a sterol precipitate separates and it is recovered from the mother liquor through filtration.

A variant to these methods is disclosed in U.S. Pat. No. 4,265,824. The unsaps are dissolved in an organic solvent, then a strong acid is added and this causes the formation of a compound with α-sitosterol and then, by cooling down the mixture causes the precipitation of β-sitosterol.

The separation of β-sitosterol and fatty alcohols, from the pitch of tall oil by means of steam distillation at high temperature, between 190 and 280° C., and the vacuum rectification of the vapor of these components have been disclosed in U.S. Pat. No. 2,866,739 of 1958 entitled Recovery of β-sitosterol from tall-oil pitch by steam distillation.

Nevertheless, such procedure can not be applied to separate the different unsap components because it has many disadvantages such as the use of steam at high temperature along with a high thermal degradation and oxidation of its valuable components.

U.S. Pat. No. 4,263,103 discloses a procedure to remove ferric ions from sterol concentrates obtained from vegetable oil or tall oil through extraction and crystallization techniques. The presence of ferric ions in sterol concentrates has a negative catalytic effect on their stability.

Accordingly, it can be seen that the fractionation through short path distillation of the complex mixture of unsaps with a content of fatty alcohols, sterols and esters of these to produce concentrates is not known in the state of the art.

The fractionation procedure of unsaps described in the present invention provides for the separation of an enriched fraction of sterols, fatty alcohols and an ester fraction. It is a highly efficient procedure and it does not use organic solvents, which is an additional advantage if we consider the increasing environmental restrictions for using organic solvents.

SUMMARY OF THE INVENTION

Raw materials for fractionation process The raw material used in the fractionation process comprises the unsaponifiable skimming fraction mainly from domestic cellulose industries (CELPAC, ARAUCO, etc.) although it can also be applied to skimmings from any origin. The unsaps can be extracted through procedures known in the state of the art. When the unsaponifiable fraction is extracted with organic solvents, this fraction must first be desolventized before fractionation. The desolventation can be carried out by application of heat at normal pressure or preferably at reduced pressure.

The raw material of the present invention can also comprise desolventized and enriched unsaps formed through the addition of one or more fractions from the same separation procedure or from any derived product or by-product. Thus, for example, the ester fraction of unsaps, once separated from these unsaps, can be hydrolyzed and such hydrolyzed product can be added to the desolventized unsaps from the skimmings. Hereafter, the term "raw material" must be understood as desolventized unsaps. When the raw material is made up of enriched unsaps as described, the term "enriched raw material" will be used.

Description of the Process

For the purposes of the present invention, the complex raw material shown in Table I can be conveniently divided into three groups of components: (1) a group that mainly comprises fatty alcohols, diterpenes, diterpenoids and unidentified substances (hereafter called "waxes" due to their physical characteristics); (2) free sterol and stanols (hereafter called "sterols"); and (3) a group mainly composed of fatty alcohol and sterol esters (hereafter called "pitch" due to the dark color caused by the presence of compounds of lignin degradation and oxidized compounds).

In the present invention, the separation of waxes, sterols and pitch from raw material is achieved by distilling the mixture in one or more short path distillation columns, also called molecular distillation columns.

To separate waxes, the raw material can be distilled under soft conditions in a system compound by a short path distillation column. If desried, a system with two or more short path distillation columns can also be used. In a multicolumn system, the distillate of the first column is used to feed a second column and the distillate of the second column is used to feed a third column and so on. The distillate becomes increasingly stripped of sterols and esters.

To separate pitch, the raw material can be distilled under mild conditions in a system composed by a short path distillation column. If desired, a system with two or more short path distillation columns can also be used. In a multicolumn system, the residue of the first column is used to feed a second column and the residue of the second column is used to feed a third column and so on. The residue becomes increasingly stripped of sterols and waxes.

One of the objectives of the present invention is to provide a method to produce an essentially sterol and pitch free wax. This method includes the steps of: (1) distilling the raw material in a short path distillation column. For this, the raw material that is solid at room temperature is melted at between 70 and 100° C. until it is liquefied. In this condition, it is fed to a short path distillation column at a temperature between 100 and 200° C. and at a pressure between 0.01 and 5 mbar. This is to produce a distillate whose weight is between 35 and 55% in weight of the feed raw material weight and to produce a residue whose weight is between 45 and 65% in weight of the feed raw material weight. The distillate contains not less than 70% in weight of free fatty alcohols in relation to the content of these alcohols in the raw material. (2) Collecting the essentially sterol and pitch free distillate or wax. To do this, the residence time of the distillate in the column is lesser than approximately 15 minutes, but it preferably lesser than 5 minutes.

Another objective of the present invention is to provide a method to produce an essentially sterol and pitch free wax. This method includes the steps of: (1) distilling the raw material in a first short path distillation column. For this, the raw material that is solid at room temperature is melted at between 70 and 100° C. until it is liquefied. In this condition, it is fed to a short path distillation column at a temperature between 200 and 300° C. and at a pressure between 0.01 and 5 mbar. This is done to produce a first distillate whose weight is between 70 and 90% in weight of the feed raw material weight and to produce a first residue whose weight is between 10 and 25% in weight of the feed raw material weight. The distillate contains not less than 70% in weight of free fatty alcohols in relation to the content of these alcohols in the raw material. To do this separation, the residence time of the distillate in the column is lesser than approximately 15 minutes, but preferably lesser than 5 minutes. (2) Collecting the first distillate. (3) Distilling the first distillate in a second short path distillation column at a temperature between 100 and 200° C. and at a pressure between 0.01 and 5 mbar. This is done to produce a second distillate whose weight is between 45 and 65% in weight in relation to the first distillate weight and a second residue whose weight is between 35 and 55% in weight in relation to the first distillate. To do this separation, the residence time of the distillate in the column is lesser than approximately 15 minutes, but it is preferred lesser than 5 minutes. (4) Collecting the second essentially sterol and pitch free distillate or wax.

Another objective of the present invention is to provide a method to produce a concentrate of sterols essentially free of wax and pitch. This method includes the steps of: (1) Distilling the raw material in a first short path distillation column. For this, the raw material that is solid at room temperature, is melted down between 70 and 100° C. until it is liquefied. In this condition, it is fed to a short path distillation column at a temperature between 200 and 300° C. and at a pressure between 0.01 and 5 mbar. This is to produce a first distillate whose weight is between 70 and 90% in weight of the feed raw material weight and to produce a first residue whose weight is between 10 and 25% in weight of the feed raw material weight. The distillate contains not less than 70% in weight of free sterols in relation to the content of these free sterols in the raw material. To do this separation, the residence time of the distillate in the first column is less than approximately 15 minutes, but it preferably less than 5 minutes. (2) Collecting the first distillate, (3) Distilling the first distillate in a second short path distillation column at a temperature between 100 and 200° C. and at a pressure between 0.01 and 5 mbar. This is to produce a second distillate whose weight is between 45 and 65% in weight in relation to the first distillate weight and a second residue whose weight is between 35 and 55% in weight in relation to the first distillate. To do this separation, the residence time of the distillate in the second column is less than approximately 15 minutes, but it is preferably less than 5 minutes. (4) Collecting the second residue which is composed of free sterols essentially free of wax and pitch, that is a sterol concentrate.

Another method to achieve the former objective includes the steps of (1) Distilling the raw material in a short path distillation column. For this, the raw material that is solid at room temperature is melted at between 70 and 100° C. until it is liquefied. In this condition, it is fed to a first short path distillation column at a temperature between 100 and 200° C. and at a pressure between 0.01 and 5 mbar. This is to produce a first distillate whose weight is between 40 and 55% in weight of the feed raw material weight and to produce a first residue whose weight is between 45 and 60% in weight of the feed raw material weight. The first residue contains not less than 70% in weight of free sterols in relation to the content of these free sterols in the raw material. To do this separation, the residence time of the distillate in the first column is lesser than approximately 15 minutes, but it is preferred lesser than 5 minutes. (2) Collecting the first residue. (3) Distilling the first residue in a second short path distillation column at a temperature between 200 and 300° C. and at a pressure between 0.01 and 5 mbar. This is to produce a second distillate whose weight is between 45 and 65% in weight in relation to the first distillate weight and a second residue whose weight is between 35 and 55% in weight in relation to the first distillate. To do this separation, the residence time of the distillate in the first column is lesser than approximately 15 minutes, but it is preferably less than 5 minutes. (4) Collecting the second distillate or free sterols essentially free of wax and pitch, that is a sterol concentrate.

Another objective of the present invention is to provide a method to produce an pitch essentially free of wax and sterols. This method includes the steps of: (1) Distilling the raw material in a short path distillation column. For this, the raw material that is solid at room temperature is melted at between 70 and 100° C. until it is liquefied. In this condition, it is fed to a short path distillation column at a temperature between 200 and 300° C. and at a pressure between 0.01 and 5 mbar. This is to produce a distillate whose weight is between 75 and 90% in weight of the feed raw material weight and to produce a residue whose weight is between 10 and 25% in weight of the feed raw material weight. (2) Collecting the essentially sterol and wax free pitch residue. To do this separation, the residence time of the distillate in the column is less than approximately 15 minutes, but it is preferably less than 5 minutes.

Another objective of the present invention is to provide a method to produce pitch essentially free of wax and sterols. This method includes the steps of: (1) Distilling the raw material in a short path distillation column. For this, the raw material that is solid at room temperature is melted down at between 70 and 100° C. until it is liquefied. In this condition, it is fed to a first short path distillation column at a temperature between 100 and 200° C. and at a pressure between 0.01 and 5 mbar. This is to produce a first distillate whose weight is between 40 and 55% in weight of the feed raw material weight and to produce a first residue whose weight is between 45 and 60% in weight of the feed raw material weight. To do this separation, the residence time of the distillate in the first column is less than approximately 15 minutes, but it is preferably less than 5 minutes. (2) Collecting the first residue. (3) Distilling the first residue in a second short path distillation column at a temperature between 200 and 300° C. and at a pressure between 0.01 and 5 mbar. This is to produce a second distillate whose weight is between 45 and 65% in weight in relation to the first distillate weight and a second residue whose weight is between 35 and 55% in weight in relation to the first distillate. To do this separation, the residence time of the distillate in the first column is less than approximately 15 minutes, but it is preferably less than 5 minutes. (4) Collecting the second residue or pitch essentially free of wax and sterols.

Another objective of the present invention is to provide a method to produce a composition of sterols and fatty acids from the pitch. This method includes the steps of: (1) Hydrolyzing the pitch obtained through the methods described above in an alkaline medium, preferably an aqueous or alcoholic solution of sodium or potassium hydroxide or pure ammonia or in an aqueous solution in presence of an organic solvent, preferably an aliphatic or aromatic hydrocarbon, at a temperature between 100 and 300° C. and for a period of time sufficient for producing the hydrolysis of pitch esters. (2) Cooling down the mixture. (3) Separating the organic phase. (4) Washing the organic phase with an aqueous solution of ethanol or methanol. (5) Desolventizing the washed organic phase to obtain a composition of free sterols and fatty alcohols. If desired, this composition can be added to the raw material to obtain enriched raw material or added to a sterol concentrate. Alternatively, the hydrolysis can be carried out without the presence of an organic solvent. In this case, once the pitch is hydrolyzed, the solvent is added, extracting the alcohols and sterols of the hydrolyzed substance, and then the method is continued as described above.

Another objective of the present invention is to provide a method to produce a sterol composition with a sterol content of not less than 90% in weight in relation to such composition weight. This method includes the steps of: (1) Mixing the sterol fraction from the second short path distillation column with acetone, methyl ethyl ketone, methanol or ethanol or a mixture thereof. (2) Agitating at room temperature or refluxing this mixture. (3) Cooling down the mixture to a temperature of approximately −20 to 20° C. (4) Separating the crystals produced during the cooling stage. (5) Desolventizing the crystals.

The described technique is normally used to crystallize sterols of raw materials with a sterol content lower than 50% in weight, although it is also applied to raw materials that have a higher sterol content.

For the sterol concentrates obtained through the methods described in the present invention, there is another method to obtain almost pure sterols which includes the steps of: (1) Mixing the concentrate with acetone or another solvent. (2) Stirring at low temperature. (3) Separating the solids from the mother liquor, for example, through filtration. (4) Desolventizing the solids, which is just a simple wash of the concentrate at a low temperature with a solvent. This process is only possible for products of the present invention, where the sterol content is so high that it is better washing them instead of recrystallizing them.

Another objective of the present invention is to provide a method to produce a fatty alcohol concentrate, between 20 and 26 carbons, with an alcohol content not lower than 75% in weight in relation to the alcohol concentrate weight. This procedure includes the steps of: (1) Mixing the wax from a first column or a second column with a solvent, preferably an aliphatic or aromatic hydrocarbon. (2) Refluxing this mixture. (3) Cooling down this mixture. (4) Separating the crystals produced during the cooling stage. (5) Desolventizing the crystals.

Another objective of the present invention is to provide a method to produce an essentially pitch free wax and free sterol mixture. This method includes the steps of: (1) Distilling the raw material in a short path distillation column. For this, the raw material that is solid at room temperature is melted at between 70 and 100° C. until it is liquefied. In this condition, it is fed to a short path distillation column at a temperature between 200 and 300° C. and at a pressure between 0.01 and 5 mbar. This is to produce a distillate whose weight is between 75 and 90% in weight of the feed raw material weight and to produce a residue whose weight is between 10 and 25% in weight of the feed raw material weight. (2) Collecting the essentially pitch free distillate. To do this separation, the residence time of the distillate in the column is less than approximately 15 minutes, but it is preferably less than 5 minutes.

Another objective of the present invention is to provide a method to produce an essentially wax and pitch free sterol concentrate. This method includes the steps of: (1) Mixing the first distillate from a first short path distillation column with acetone, methyl ethyl ketone, methanol or ethanol or a mixture thereof. (2) Refluxing the mixture. (3) Cooling down the mixture to a temperature of approximately −20 to 20° C. (4) Separating the crystals produced during the cooling stage. (5) Desolventizing the crystals.

Another objective of the present invention is to provide a method to produce an essentially sterol and pitch free wax concentrate. This method includes the steps of: (1) Mixing the first distillate of a first short path distillation column with acetone, methyl ethyl ketone, methanol or ethanol or a mixture thereof. (2) Refluxing the mixture. (3) Cooling down the mixture to a temperature of approximately −20 to 20° C. (4) Separating the crystals produced during the cooling stage. (5) Desolventizing the mother liquor to recover a wax concentrate.

Another objective of the present invention is to provide a method to produce an essentially sterol and pitch free fatty alcohols. This method includes the steps of: (1) Mixing the first distillate of a first short path distillation column with acetone, methyl ethyl ketone, methanol or ethanol or a mixture thereof. (2) Refluxing the mixture. (3) Cooling down the mixture to a temperature of approximately −20 to 20° C. (4) Separating the crystals produced during the cooling stage. (5) Desolventizing the mother liquor. (6) Dissolving the residual solid of the disolvenation stage with hexane, heptane, toluene, xylene or a mixture thereof. (7) Refluxing this mixture. (8) Cooling down the mixture to a temperature of approximately between −20 and 20° C. (9)

Separating the crystals produced during the cooling stage. (10) Desolventizing the crystals.

Another objective of the present invention is to provide a method to produce an essentially wax and pitch free sterol concentrate. This method includes the steps of: (1) Mixing the first residue of a first short path distillation column with acetone, methyl ethyl ketone, methanol or ethanol or a mixture thereof (2) Agitating at room temperature or refluxing the mixture. (3) Cooling down the mixture to a temperature of approximately −20 to 20° C. (4) Separating the crystals produced during the cooling stage. (5) Desolventizing the crystals.

Another objective of the present invention is to provide a method to produce an essentially wax and sterol free pitch. This method includes the steps of: (1) Mixing the first residue of a first short path distillation column with acetone, methyl ethyl ketone, methanol or ethanol or a mixture thereof. (2) Refluxing the mixture. (3) Cooling down the mixture to a temperature of approximately −20 to 20° C. (4) Separating the crystals produced during the cooling stage. (5) Desolventizing the mother liquor to obtain a pitch concentrate.

The pitch obtained through the methods described in the present invention can be conveniently purified or bleached to obtain an ester concentrate suitable for an alimentary utilization.

For that, the dark colored pitch can be distilled in a short path distillation column with the evaporator at a temperature of or higher than 250° C. and the condenser at a temperature between 150 and 200° C. and a pressure between 0.01 and 5 mbar. It has been surprisingly discovered that the distillate is light or it has a light amber color in those conditions, and the dark, oxidized or degraded matter remains in the column residue.

Another way to purify or bleach the pitch is the adsorption of the dark impurities with activated carbon or another adsorbent. The methods to carry out the bleaching are going to be described in the examples.

Of course, if desired, the pitch can also be bleached prior to its hydrolysis to produce free sterols, stanols or fatty alcohols.

The terms "essentially free" are understood as follows:

Essentially pitch free wax: Fraction of the raw material with a content of fatty alcohol esters and sterol esters lower than 20% in weight of esters in relation to the content of these esters in the raw material and a content of fatty alcohols not lower than 70% in weight of these alcohols in relation to the content of these alcohols in the raw material.

Essentially sterol free wax: Fraction of the raw material with a content of free sterols lower than 20% in weight of free sterols in relation to the content of sterols in the raw material and a content of fatty alcohols not lower than 70% in weight of these alcohols in relation to the content of these alcohols in the raw material.

Essentially pitch free sterols: Fraction of the raw material with a content of fatty alcohol esters and sterol esters lower than 20% in weight of esters in relation to the content of these esters in the raw material and a content of free sterols and stanols not lower than 70% in weight of these free sterols and stanols in relation to the content of these free sterols in the raw material.

Essentially wax free sterols: Fraction of the raw material with a content of free fatty alcohols lower than 20% in weight of these alcohols in relation to the content of these alcohols in the raw material and a content of free sterols and stanols not lower than 70% in weight of these free sterols and stanols in relation to the content of these free sterols in the raw material.

Essentially wax free pitch: Fraction of the raw material with a content of free fatty alcohols lower than 20% in weight of these free alcohols in relation to the raw material and a content of alcohol and sterol esters not lower than 70% in weight of these alcohols in relation to the content of these alcohols in the raw material.

Essentially sterol free pitch: Fraction of the raw material with a content of free sterols and stanols lower than 20% of the content of these free sterols and stanols in relation to the content of these free sterols and stanols in the raw material and a content of fatty alcohol and sterol esters not lower than 70% in weight of these alcohols in relation to the content of these alcohols in the raw material.

BRIEF DESCRIPTION OF THE DRAWINGS

These and other features, aspects, object and advantages of the present invention will become better understood upon consideration of the following detailed description, appended claims and accompanying drawing where:

It should be understood that the drawings are not necessarily to scale and that the embodiments are sometimes illustrated by graphic symbols, phantom lines, diagrammatic representations and fragmentary views. In certain instances, details that are not necessary for understanding the invention or which make other details difficult to perceive may have been omitted. It should be understood, of course, that the invention is not necessarily limited to the particular embodiments illustrated herein.

DETAILED DESCRIPTION OF THE INVENTION

The present invention uses what is known as a short path distillation column or a molecular distillation column that efficiently separates the complex mixture of neutral compounds of the raw material in wax, concentrating free sterols and pitch. In a conventional vacuum distillation column, the distance between the evaporation and condensation surface is much longer than the mean free path of molecules at operation pressure. The device generally consists of a reboiler, a fractionation column and a condenser operating at low vacuum. In a molecular distillation column, the vapor path to reach the condenser is not obstructed because a distance that is shorter than the mean free path of molecules that distill separates the condenser from the evaporator. Usually, the mean free path of molecules has a few centimeters in a molecular distillation column. Nevertheless, in order to reach higher rates of distillation, the distance between the evaporation surface and the condensation surface is slightly higher than the distance of the mean free path. Short path distillation columns where the evaporation surface and condensation surface are near, are adequate to the objectives of the present invention. When it is said that such surfaces are near, it means that the distance between those surfaces is less than approximately 100 centimeters (it is preferred between 3 and 50 centimeters, approximately).

The operation system of a short path distillation column is very similar in many aspects to the operation system of a molecular distiller.

Falling film short path distillation columns with or without scraper, short path distillation column-centrifuges, multistage short path distillation columns and others are adequate types of columns for the purposes of the present invention.

Figure 1:
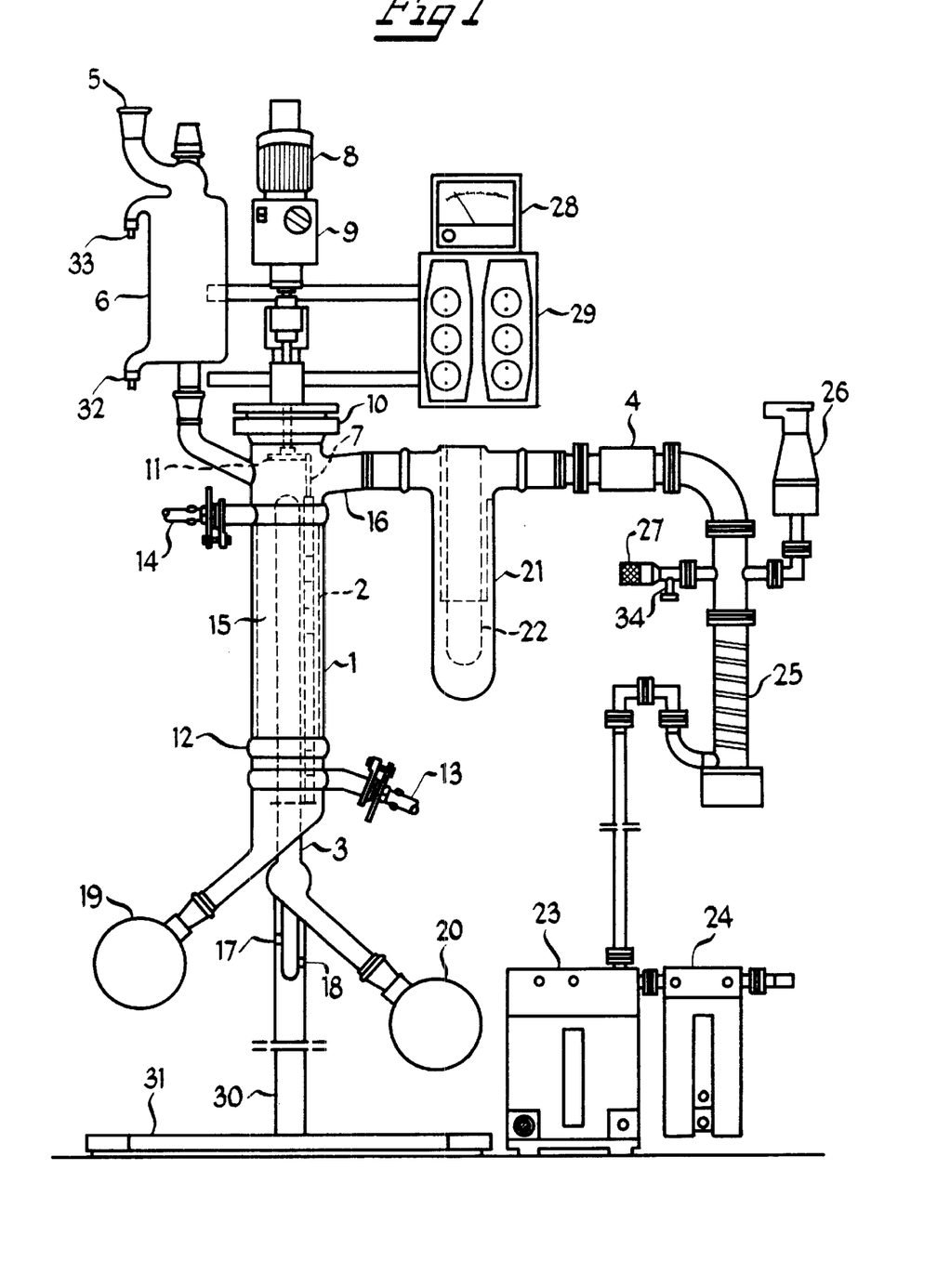
FIG. 1 shows a short path distillation column with scrapers and the auxiliary equipment used in the present invention.

FIG. 1 shows a short path distillation column with scrapers and the auxiliary equipment used in the present invention. It is available in UIC GmbH and its American subsidiary UIC Inc. Of course, other short path distillation columns or evaporators can also be used. Now the present invention can be explained through FIGS. 1, 2 and 3.

FIG. 1 shows a short path distillation column 1 with an evaporation surface 2 located near to a hollow internal condenser 3 in which a thermal fluid runs that enters via line 17 and exits via line 18. The source of this heat transfer fluid is not shown. The raw material 5 is fed from the top to a double wall graduated dispenser 6 provided with an entrance 32 and an exit 33 for a transfer fluid, which maintains the raw material in liquid state. The heating fluid source is not shown. The raw material runs down to the evaporator surface 2 and a rotary scraper distributor 7 spreads the raw material 5 on the surface. A motor 8 provided with a speed control device that is near to the top of the evaporator 1 by flange 10 makes the shaft 11 and the dispenser-scraper rotate 7. The combined effect of gravity and the dispenser-scraper 7 allows a thin and uniform layer to cover the evaporator surface 2. The thin layer is heated on the evaporator surface by circulating a heat transfer fluid through the jacket 12. The heat transfer fluid enters via line 13 and exits via line 14. The source of the heat transference fluid is not shown. Heat transference fluid temperature in the column 1 jacket 12 is 50° C. lower than heat transfer fluid temperature in the inner condenser 3 of the column 1. An adequate heat transference fluid could be water, pressure water, steam, ethylenglicol, oil, special or similar thermal fluids.

The space 15 between the evaporator surface 2 and the inner condenser 3 is evacuated by vacuum line 16 connected to a double wall cold trap 21. Inside of it 21, there is a cooling device (liquid air or dry ice with isopropanol, for example). The combination of vacuum and heat allows volatile components to escape from the thin layer, to travel on the space 15, and to condense on the inner condenser 3. More volatile components are retailed in the cold trap. The distillate that is not shown runs down on the evaporator surface 2 as a thin layer and arrives the flask 19. The distillate that is not shown runs down on outer surface of the inner condenser 3 and arrives the flask 20. As the thin film runs down, it gets rich in pitch or in pitch plus sterols. The vacuum in space 15 is produced by a rotary vane vacuum pump 23 provided with an exhaust gas filter and connected to the cold trap 21 exit 4 through a diffusion pump 25. A pressure sensor 26 sends an electric signal to a pressure meter, which indicates the pressure present in the space 15. A micrometric valve 27 located at the entry of the diffusion pump 25 allows regulating pressure by the controlled entrance of air 34. Column 1 and its accessories are fixed to a metallic bearing 30 over a base 31. An electric panel 29 contains the connections for the pressure sensor 26, the motor 8, the diffusion pump 25, the vacuum rotary pump 23 and the thermostats for the heat transfer fluids.

Using a distillation system that contains only one short path distillation column as shown in FIG. 1, the distilled fraction generally consists of wax or wax with free sterols.

When the distilled fraction collected on the flask 20 consists of wax with free sterols, this fraction can be fed to another short path distillation column (See FIG. 2) to produce an essentially free sterol free distilled fraction and an essentially wax free residue.

When the distilled fraction collected on flask 20 in the first column essentially consists of wax, the collected residue on flask 19 can be fed to a second short path distillation column (See FIG. 3) to produce an essentially pitch free distilled fraction and an essentially free sterol free residue.

One short path distillation column system is usually preferred. However, in some cases, the use of two or more short path distillation columns is preferred. The use of multiple short path distillation columns is illustrated in FIGS. 2 and 3.

Figure 2:
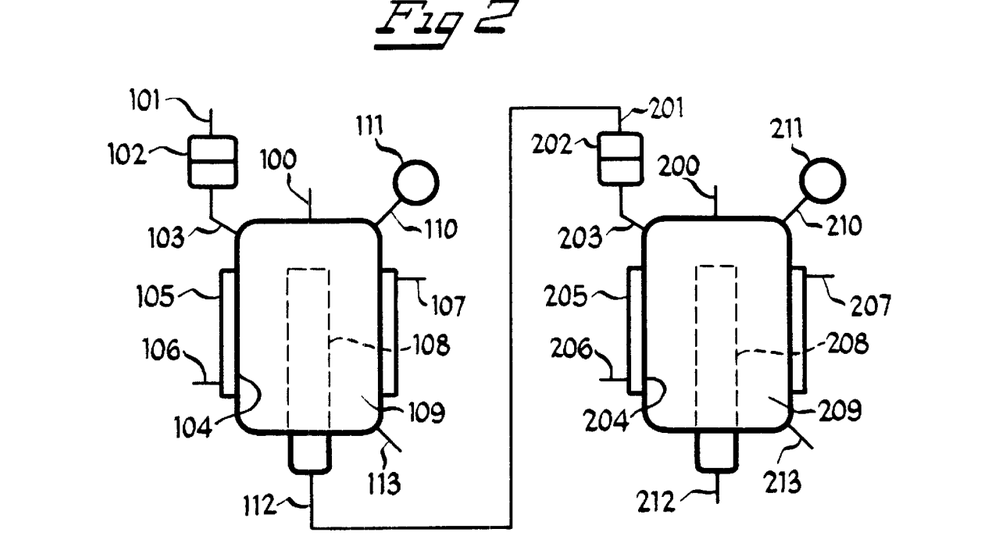
FIG. 2 shows an example of the use of multiple short path distillation columns.

In FIG. 2, each column 100 and 200 are short path distillation columns diagrammatically illustrated and they can be similar to the column of FIG. 1. Through line 101 the raw material is fed to the accumulator-dispenser vessel 102 of the column 100. Through line 103 the raw material is fed to the top of column 100 in a way that it flows as a layer on the surface 104 of column 100. A dispenser-scraper system (not shown) can be used as shown in FIG. 1 to assured a uniform distribution on the column surface. Column 100 has a jacket 105 to transfer heat to the column surface 104 through a heat transference fluid that is fed to the jacket 105 through line 106 and is evacuated though line 107. Also, the column has an inner condenser 108 that is next to the surface 104 and separated by the space 109. Through the vacuum pump 111 vacuum is applied to space 109 through line 110. The distillate flows through the condenser 108 to leave the column 100 through line 113. In turn, the distillate or the bottom of distillation flows through the surface 104 to leave the column through line 112.

The distillate or top of column 100 is carried through line 113 to accumulator-dispenser basin 202 of column 200. Through line 203 the distillate of column 100 is fed to the top of column 200 in a way that it flows as a layer on the surface 204 of column 200. A dispenser-scraper system (not shown) can be used as shown in FIG. 1 to assured a uniform distribution on the column surface. Column 200 has a jacket 205 to transfer heat to the column surface 204 through a heat transference fluid that is fed to the jacket 205 through line 206 and is evacuated though line 207. Also, the column has an inner condenser 208 that is next to the surface 204 and separated by the space 209. Through the vacuum pump 211 vacuum is applied to space 209 through line 210. The distillate flows through the condenser 208 to leave the column 200 through line 213. In turn, the distillate or distillate bottom flows through the surface 204 to leave the column through line 212.

Figure 3:
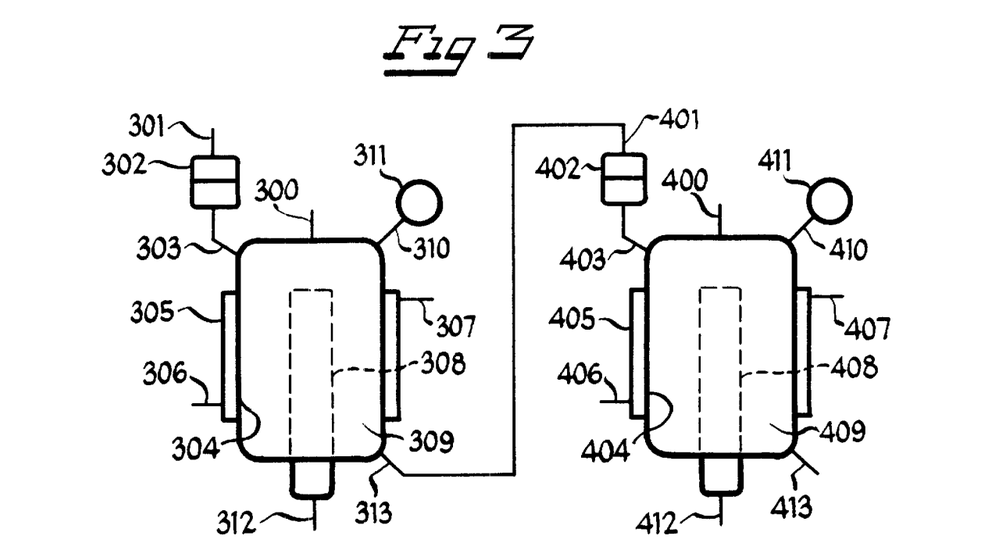
FIG. 3 shows an example of the use of multiple short path distillation columns.

In FIG. 3, each column 300 and 400 are short path distillation columns diagrammatically illustrated and they can be similar to the column of FIG. 1 or they can have another design of short path evaporation column. Through line 301 the raw material is fed to the accumulator-dispenser basin 302 of the column 300. Through line 303 the raw material is fed to the top of column 300 in a way that it flows as a layer on the surface 304 of column 300. A dispenser-scraper system (not shown) can be used as shown in FIG. 1 to assured a uniform distribution on the column surface. Column 300 has a jacket 305 to transfer heat to the column surface 304 through a heat transference fluid that is fed to the jacket 305 through line 306 and is evacuated though line 307. Also, the column has an inner condenser 308 that is next to the surface 304 and separated by the space 309.

Through the vacuum pump 311 vacuum is applied to space 309 through line 310. The distillate flows through the condenser 308 to leave the column 300 through line 312. In turn, the distillate or bottom of the column flows through the surface 304 to leave the column through line 313.

The distillate or distillation bottom of column 300 is carried through line 313 to accumulator-dispenser basin 402 of column 400. Through line 403 the distillate of column 300 is fed to the top of column 400 in a way that it flows as a layer on the surface 404 of column 400. A dispenser-scraper system (not shown) can be used as shown in FIG. 1 to assured a uniform distribution on the column surface. Column 400 has a jacket 405 to transfer heat to the column surface 404 through a heat transference fluid that is fed to the jacket 405 through line 406 and is evacuated though line 407. Also, the column has an inner condenser 408 that is next to the surface 404 and separated by the space 409. Through the vacuum pump 411 vacuum is applied to space 409 through line 410. The distillate flows through the condenser 408 to leave the column 400 through line 413. In turn, the distillate or bottom of the column flows through the surface 404 to leave the column through line 412.

The following examples that illustrate the present invention with more details do not limit it. The analytical techniques used are described after the examples.

In the following examples, a raw material containing approximately 52% of wax, 33% of free sterols and 15% of pitch or esters has been used.

EXAMPLE 1

Production of wax 94 gr. of melted raw material were loaded in a graduated dispenser of a short path distillation column illustrated in FIG. 1. The dispenser temperature was maintained at 80° C. through water circulation in the jacket. Column jacket temperature was maintained at 150° C. through circulation of mineral oil at that temperature. The condenser temperature was 80° C. Once the column pressure reached 0.1 mbar (absolute pressure), the column was fed at approximately 1 ml. per minute and the distributor-scraper rotated at a speed of 200 r.p.m. Once the operation finished, a 40.4 gr. distillate were collected i.e. 43% in weight of the fed raw material. The collected mass in the cold trap was of 2% in weight of the feeding.

The distillate composition was of 95% of waxes and 3.8% of sterols. In the wax fraction, approximately 94% of feeding docosanol and 91% of feeding tetracosanol are found.

EXAMPLE 2

Production of pitch 104 gr. of raw material were loaded in short path distillation column dispenser at 80° C. The column evaporator temperature was of 230° C. and the condenser temperature was of 195° C. The pressure was of 0.1 mbar and the column was fed at approximately 1 ml. per minute and the distributor-scraper rotated at a speed of 200 r.p.m.. At the end of the operation, the collected mass on the cold trap was 6.1% in weight of the fed mass and the distillate mass was 76.1% in weight of the fed raw material mass. The pitch or residue was 17.8% in weight of the fed raw material mass and it had approximately 81% of sterol esters and fatty alcohols, 18% of sterols and 1% of waxes.

EXAMPLE 3

Production of wax and free sterols 50 gr. of Example 2 distillate were loaded in a short path distillation column dispenser. The dispenser temperature was maintained at 95%. The column evaporator temperature was of 150° C. and the condenser temperature was of 80° C. The operation pressure was of 0.1 mbar and the feeding rate was approximately of 1 ml per minute and the distributor-scraper rotated at a speed of approximately 200 rpm. The collected distillate represented 50.6% in feeding weight and had a wax composition of 90% and sterol composition of 10%. The fatty alcohols corresponded approximately to 70% of total fed fatty alcohols. In the distillate or distillation bottom, approximately 87% of fed sterols are found. Mass in the cold trap was not recovered.

EXAMPLE 4

Production of sterols and pitch 43 gr. of Example 1 residue were loaded in a short path distillation column dispenser at 100° C. and fed to the column evaporator at 1 ml per minute. The evaporator temperature was of 230° C., the condenser temperature was of 145° C., the column pressure was of 0.1 mbar and the distributor-scraper rotated at a speed of approximately 200 rpm. At the end of the operation, the collected distillate weighed 29 gr. representing 67.4% in weight of the fed mass and the residue weighed 14 gr representing 32.6% in weight of the fed mass. No distillate was recovered from the cold trap. The top current has approximately 92% of fed sterols and the bottom mass has a 90% of sterol esters and fatty alcohols.

EXAMPLE 5

Pitch hydrolysis 100 gr. of pitch produced as described in Example 4 are used with a free sterol content of approximately 5.2% in weight. They were mixed with 300 gr. of a methanolic solution of KOH at 15% with 300 gr. of toluene and they were loaded to a Parr pressure reactor, model 4522. Here, they were left to react under agitation at 252° C. and 58 bar for three hours. Once the reactor content cooled down, the mixture was poured to a separator recovering the superior organic phase. This phase was mixed with 50 ml of an aqueous ethanolic solution 1:1 in volume and was vigorously agitated for a few minutes pouring to a separator. This operation was repeated until the aqueous solution resulting from the washing of the organic phase had a neutral pH. The separated organic phase was desolventized. The recovered solids weighed 92.7 gr. and their composition was: free sterols, 43.2%; fatty alcohols, 19%; fatty acids, 36%.

EXAMPLE 6

Obtaining fatty alcohol concentrate 55 gr. of waxes obtained as described in Example 1 were mixed with 250 ml of hexane, and they were heated and refluxed for 15 minutes. After this, they were left to cool down at a speed of approximately 1° C. per minute until 5° C. The crystallized mixture was filtered in a Kitasato flask under vacuum in a Büchner filter using Whatman filter paper N°5. The crystals were desolventized in a vacuum oven at 1 mbar and 100° C. for 6 hours. The crystals obtained through this procedure have a fatty alcohol content of 90% with the following purity:

TABLE 3

Relative purity of fatty alcohols obtained from the wax

| Compound | % Relative |
| --- | --- |
| Eicosanol | 5.9 |
| Docosanol | 52.0 |
| Tetracosanol | 30.0 |
| Hexacosanol | 1.2 |
| Sterols | 8.0 |

EXAMPLE 7

Production of a free sterol composition 1

25 gr. of a sterol concentrate produced as described in Example 3 were mixed with 95 ml of acetone and refluxed for 15 minutes. After this, they were left to cool down at a cooling speed of approximately 1° C. per minute until 5° C. The crystallized mixture was filtered in a Kitasato flask under vacuum in a Büchner filter using Whatman filter paper N°5. The crystals were desolventized in a vacuum oven at 1 mbar and 100° C. for 6 hours. The crystals obtained through this procedure have a sterol purity of 92.7%.

EXAMPLE 8

Production of a free sterol composition 2

15 gr. of a sterol concentrate produced as described in Example 4 were mixed with 40 ml of acetone at a temperature of −5° C. in a 100-ml erlenmeyer flask. The mixture was agitated for 5 minutes by a magnetic agitator. Then, the mixture was filtered in a Kitasato flask under vacuum in a Büchner filter using Whatman filter paper N°5. The crystals were desolventized in a vacuum oven at 1 mbar and 100° C. for 6 hours. The solids obtained have a sterol purity of 87%.

EXAMPLE 9

Purification of wax and sterol concentrate 30 gr. of the top flow generated as described in Example 2 were mixed with 60 gr. of methanol and refluxed for 15 minutes. After this, they were left to cool down at a cooling speed of approximately 1° C. per minute until 5° C. The crystallized mixture was filtered in a Kitasato flask under vacuum in a Büchner filter using Whatman filter paper N°5. The crystals obtained through this procedure have a sterol purity of 77%.

EXAMPLE 10

Purification of wax filtrate

The methalonic mother liquor resulting from filtration as described in Example 9 was disolventized and cool down in a vacuum dryer. The resulting mass was dissolved in a proportion of solid: hexane=1:1 and was refluxed for 15 minutes. After this, it was left to cool down at a cooling speed of approximately 1° C. per minute until 5° C. The crystallized mixture was filtered in a Kitasato flask under vacuum in a Büchner filter using Whatman filter paper N°5. The crystals obtained through this procedure have a docosanol purity of 47% and a tetracosanol purity of 21%.

EXAMPLE 11

Purification of sterol and pitch concentrate 45 gr. of the bottom flow generated as described in Example 1 were mixed with 150 ml of methyl ethyl ketone and refluxed for 15 minutes. After this, it was left to cool down at a cooling speed of approximately 1° C. per minute until 0° C. The crystallized mixture was filtered in a Kitasato flask under vacuum in a Büchner filter using Whatman filter paper N°5. The crystals obtained through this procedure have a sterol purity of 81%.

EXAMPLE 12

Hydrolysis of pitch filtrate

The mother liquor resulting from filtration as described in Example 11 was disolventized and cooled down in a vacuum dryer. The resulting mass has 52% of esters and 45% of sterols. 10 gr. of the mass were used and dissolved with 40 gr. of a methalonic solution of KOH at 15% and 40 gr. of toluene and then they were loaded to a Parr pressure reactor model 4522. Here, they left to react under agitation at 254° C. and 59 bar for three hours. Once the reactor content cooled down, the mixture was poured to a separator recovering the superior organic phase. This phase was mixed with 25 ml of an aqueous ethanolic solution 1:1 in volume and was vigorously agitated for a few minutes pouring to a separator. This operation was repeated until the aqueous solution resulting from washing of the organic phase had a neutral pH. The separated organic phase was desolventized. The recovered solids weighed 9.6 gr. and their composition was free sterols, 67%; fatty acids, 10%.

EXAMPLE 13

Purification of pitch 1

25 gr. of pitch concentrate obtained as described in example 2 were loaded to a short path distillation column dispenser at 200° C. heated with mineral oil. The evaporator temperature was of 250° C., the condenser temperature was of 200° C., the column pressure was of 0.1 mbar and the feeding rate was 1 ml per minute. The distributor-scraper rotated at a speed of approximately 200 rpm. At the end of the operation, the collected mass weighed 24 gr. representing 97%. The mass had a light amber color, notably less intense than the dark color fed mass.

EXAMPLE 14

Purification of pitch 2

35 gr. of pitch concentrate obtained as described in example 4 were dissolved at 5% with chloroform at room temperature, obtaining a black solution. The solution was eluated through a 15-mm-diameter and 30-cm-long glass column with porous frit that was half loaded with chloroform soaked up alumina at 10 ml per minute and at room temperature. The orange-colored yellow resulting solution was dessolventized in a Büchi rotary evaporator model R-124V at 10 mbar. The resulting mass has a crystalline amber color.

Description of the analytical technique: Chromatographic Analysis

The identification of the unsaponifiable components and the unsaponifiable fractions obtained according to the procedure of the present invention was carried out through a gaseous capillar chromatography. The chromatographic method used is the result of an extensive survey about the more convenient conditions and techniques for determining the different components in the unsaponifiables and the unsaponifiable fractions.

a) Chromatographic operation parameters

Hewlett Packard chromatographer, model HP 5890, series 2, capillary column HP-5, 30 m long, 0.32 mm diameter, 0.25 mm film

| | |
|---|---|
| Oven temperature | 300° C. (isotherm) |
| Injector temperature | 320° C. |
| Detector temperature | 320° C. |
| Carrier flux (He) | 0.92 ml/min |
| Split | 60:1 |
| Program | Isotherm, 15 min |
| Injection | 0.5 $\mu$l | a) Sample preparation

Weigh 100 mgr. of the sample in a 25-ml gaged flask

Completely dissolve with tetrahydrofurane (THF) and grade

Exactly add 500 $\mu$l of this solution in a silylation tube

Weight 50 mgr of 5$\beta$-colestan-3$\beta$-ol in a 100-ml gaged flask

Completely dissolve with n-propanol and grade

Exactly add in the silylation tube 500 $\mu$l of the 5$\beta$-colestan-3$\alpha$-ol solution Dry under nitrogen atmosphere at soft heating Add 300 $\mu$l of Bis(trimethylsilyl)trifluoroacetamide (BSTFA)

Add 300 $\mu$l of pyridine

Maintain the solution at 70° C. for 10 minutes

Dry under inert atmosphere at soft heating

Dissolve with 500 $\mu$l of THF

Note: The reagents must have analytic grade a) Calculations

Record the area of the compound of interest

Record the area of 5$\beta$-colestan-3$\alpha$-ol

Calculate the weight percentage of the compound of interest through the following formula:

$$\% X = \frac{A_x \cdot M_p}{A_p \cdot M_m} \cdot 100$$

Where

X: percentage in weight of the compound of interest $A_x$: chromatographic area of the compound of interest $M_p$: pattern added mass (5$\beta$-colestan-3$\alpha$-ol)

$A_p$: pattern chromatographic area (5$\beta$-colestan-3$\alpha$-ol)

$M_m$: sample added mass

Although the invention has been described in considerable detail with reference to certain preferred versions, one skilled in the art will appreciate that the present invention can be practiced by other than the preferred versions, which have been presented for the purpose of illustration and not of limitation. Therefore, the spirit and scope of the appended claims should not be limited to the description of the preferred versions provided herein.

What is claimed is:

1. A process for the recovery of sterols, esters and wax alcohols from mixtures of neutral matter obtained from black liquor soap skimmings comprising:

(a) feeding the mixture of neutral matter to a first short path distillation column so as to form a first fraction comprising wax alcohols and a second fraction comprising sterols and esters;

(b) recovering said first and second fractions;

(c) feeding said second fraction to a second short path distillation column so as to form a third fraction comprising sterols and a fourth fraction comprising esters;

(d) recovering said third and fourth fractions.

2. The process according to claim 1, wherein the pressure in the first short path distillation column is within the range of about 0.01 mbar to about 5 mbar and the temperature of the evaporation surface of said column is within the range of about 100° C. to about 200° C. and the temperature of the condenser surface is within the range of about 60° C. to about 100° C. and the distance between the evaporation surface and the condenser surface of said column is less than 50 cm.

3. The process according to claim 2, wherein the pressure in the second short path distillation column is within the range of about 0.01 mbar to about 5 mbar and the temperature of the evaporation surface of said column is within the range of about 200° C. to about 250° C. and the temperature of the condenser surface is within the range of about 100° C. to about 180° C. and the distance between the evaporation surface and the condenser surface of said column is less than 50 cm.

4. The process according to claim 2, comprising:

dissolving the first fraction so as to form a solution, in a solvent selected from the group consisting of petroleum ether, hexane, heptane, benzene, toluene, xilene or mixtures of two or more of these solvents;

cooling the solution so as to from a precipitate and mother liquor;

separating the precipitate from the mother liquor so as to form a mixture of long chain aliphatic alcohols comprising 20 to 26 atoms per molecule.

5. The process according to claim 4 wherein the mixture comprises not less than 70% in weight of docosanol and tetracosanol.

6. The process according to claim 3 comprising:

dissolving the third fraction so as to form a solution, in a solvent selected from the group consisting of acetone, methyl ethyl ketone, dialkyl ketone comprising 3 to 10 carbon atoms per molecule, methanol, ethanol, or mixtures of two or more of these solvents;

cooling the solution so as to from a precipitate and mother liquor;

separating the precipitate from the mother liquor so as to form a mixture comprising non-esterified sterols and stanols.

7. A process according to claim 6 wherein the mixture comprises not less than 90% in weight of non-esterified sterols and stanols.

8. The process according to claim 3 comprising:

mixing the fourth fraction with an aqueous solution of sodium or potassium or ammonium hydroxide and a solvent selected from the group consisting of toluene, xilene or hexane;

heating the mixture at a temperature not exceeding 300° C.;

cooling the heated mixture;

separating an aqueous phase and an organic phase;

desolventizing the organic phase so as to from a solid mixture comprising non-esterified sterols, stanols or fatty alcohols.

9. A process for the recovery of sterols, esters and wax alcohols from mixtures of neutral matter obtained from black liquor soap skimmings comprising:

(a) feeding the mixture of neutral matter to a first short path distillation column so as to form a first fraction comprising esters and a second fraction comprising wax alcohols and sterols;

(b) recovering said first and second fractions;

(c) feeding said second fraction to a second short path distillation column so as to form a third fraction comprising wax alcohols and a fourth fraction comprising sterols;

(d) recovering said third and fourth fractions.

10. The process according to claim 9, wherein the pressure in the first short path distillation column is within the range of about 0.01 mbar to about 5 mbar and the temperature of the evaporation surface of said column is within the range of about 200° C. to about 250° C. and the temperature of the condenser surface is within the range of about 100° C. to about 180° C. and the distance between the evaporation surface and the condenser surface of said column is less than 50 cm.

11. The process according to claim 10, wherein the pressure in the second short path distillation column is within the range of about 0.01 mbar to about 5 mbar and the temperature of the evaporation surface of said column is within the range of about 100° C. to about 200° C. and the temperature of the condenser surface is within the range of about 60° C. to about 100° C. and the distance between de evaporation surface and the condenser surface of said column is less than 50 cm.

12. The process according to claim 10 comprising:

mixing the first fraction with an aqueous solution of sodium or potassium or ammonium hydroxide and a solvent selected from the group consisting of toluene, xilene or hexane;

heating the mixture at a temperature not exceeding 300° C.;

cooling the heated mixture;

separating an aqueous phase and an organic phase;

desolventizing the organic phase so as to from a solid mixture comprising non esterified sterols, stanols or fatty alcohols.

13. The process according to claim 11 comprising:

dissolving the third fraction so as to form a solution, in a solvent selected from the group consisting of petroleum ether, hexane, heptane, benzene, toluene, xilene or mixtures of two or more of these solvents;

cooling the solution so as to from a precipitate and mother liquor;

separating the precipitate from the mother liquor so as to form a mixture of long chain aliphatic alcohols comprising 20 to 26 atoms per molecule.

14. The process according to claim 13 wherein the mixture comprises not less than 70% in weight of docosanol and tetracosanol.

15. The process according to claim 11 comprising:

dissolving the fourth fraction so as to form a solution, in a solvent selected from the group consisting of acetone, methyl ethyl ketone, dialkyl ketone comprising 3 to 10 carbon atoms per molecule, methanol, ethanol, or mixtures of two or more of these solvents;

cooling the solution so as to from a precipitate and mother liquor;

separating the precipitate from the mother liquor so as to form a mixture comprising non-esterified sterols and stanols.

16. A process according to claim 14 wherein the mixture comprises not less than 90% in weight of non esterified sterols and stanols.

* * * * *